United States Patent
Sobolev et al.

(10) Patent No.: US 6,500,800 B1
(45) Date of Patent: Dec. 31, 2002

(54) COMPOSITION AND METHOD FOR CAUSING PHOTODYNAMIC DAMAGE TO TARGET CELLS

(76) Inventors: Alexander Sergeevich Sobolev, 117192, ul. Vinnitskaya, d 13, kv.120, Moscow (RU); Andrei Alexandrovich Rozenkrants, 117133, ui. Akademika Vargi, d.8, kv.49, Moscow (RU); Tamara Vladimirovna Akhlynina, 109117, ul. Zhigulevskaya, d.12, korp. 5,kv.54, Moscow (RU); David Andrew Jans, 103064, Gorokhovsky per. d. 4, kv120, Moscow (RU)

( * ) Notice: Subject to any disclaimer, the term of this patent is extended or adjusted under 35 U.S.C. 154(b) by 0 days.

(21) Appl. No.: 09/125,164

(22) PCT Filed: Feb. 3, 1997

(86) PCT No.: PCT/RU97/00018

§ 371 (c)(1), (2), (4) Date: Aug. 12, 1998

(87) PCT Pub. No.: WO97/28822

PCT Pub. Date: Aug. 14, 1997

(30) Foreign Application Priority Data

Feb. 12, 1996 (RU) .......................................... 96102402

(51) Int. Cl.⁷ ........................ A61K 31/40; A61K 35/76; A61K 39/385; A61K 41/00; A61K 47/42
(52) U.S. Cl. ........................ 514/3; 424/9.61; 514/21; 514/410; 530/303; 530/345; 530/362; 530/409; 530/410; 540/145
(58) Field of Search .............................. 514/12, 3, 21, 514/410, 422; 530/350, 303, 324, 845, 362, 408, 409, 410; 424/9.6, 9.61; 540/122, 145

(56) References Cited

U.S. PATENT DOCUMENTS

| 4,771,130 A | | 9/1988 | Cohen ........................ 514/866 |
| 5,238,940 A | * | 8/1993 | Liu et al. ..................... 514/410 |
| 5,599,831 A | * | 2/1997 | Poretz et al. ................ 514/410 |

FOREIGN PATENT DOCUMENTS

| EP | 279757 A | * | 8/1988 |
| WO | 95/32001 | | 11/1995 |

OTHER PUBLICATIONS

Akhlynina et al. Insulin–Mediated Intracellular Targeting ... Cancer Research. vol. 55, pp. 1014–1019, Mar. 1, 1995.*

(List continued on next page.)

*Primary Examiner*—Jeffrey E. Russel
(74) *Attorney, Agent, or Firm*—Knobbe, Martens, Olson & Bear, LLP (57) ABSTRACT

The present invention is directed to a composition for causing photodynamic damage to target cells comprising a photosensitiser, a photosensitiser carrier component, a component which enables target cell recognition and transport of the photosensitiser toward the interior of the target cell by specific receptor-mediated endocytosis, and a component capable of effective targeted transport of the photosensitiser within the target cells. The invention is also related to a method for causing photodynamic damage to target cells comprising the steps of: adding the composition to the cells; keeping the cells at a temperature of normal vital activity of cells with the composition for causing photodynamic damage to the target cells, said composition comprising the above-mentioned components; and exposure of the cells to light.

17 Claims, 4 Drawing Sheets

OTHER PUBLICATIONS

Akhlynina et al., "The Use of Internalizable Derinatines of Chlorin $E_6$ for Increasing its Pholosensitizing Activity Photochemistry and Photobiology," vol. 58, No. 1, pp. 45–48, 1993.*

Soboler et al., "Internalizable Insulin–BSA–Chlorin $E_6$ Conjugate is a more Effective Photosensitizer than Chlorin E6 Alone," Biochemistry International vol. 26, No. 3, Mar. 1992, pp. 445–450.*

T.V. Akhlynina, et al.; Bulletin of Experimental Biology and Medicine (Moscow); 109: 150–152 (1990); *Photodynamic Action of Concanavalin A–Chlorine $e_6$ Conjugate on Human Fibroblasts*.

* cited by examiner

COMPOSITION AND METHOD FOR CAUSING PHOTODYNAMIC DAMAGE TO TARGET CELLS

CROSS REFERENCES TO RELATED APPLICATIONS

This is the U.S. national phase under 35 U.S.C. §371 of International Application PCT/RU97/00018, filed Feb. 3, 1997, which claims priority to Russian Federation Application 96102402/13, filed Feb. 12, 1996.

BACKGROUND OF THE INVENTION

1. Field of the Invention

The present invention relates to biotechnology, cellular and molecular biology and, more particularly, to a method for causing photodynamic damage to target cells which may be used in experimental medicine and pharmacology.

2. Description of Related Art

The essence of the photodynamic therapy consists in the introduction to the organism of a photosensitiser (hereinafter referred to as "PS") taken up practically by all cells. Due to differences in microcirculation, distribution, exchange intensity and so on, the PS remains a longer time in target cells, for example cancer cells, than in normal cells. If at that time, target cells and PS molecules occurring therein are exposed to light, the latter shall cause photochemical reactions resulting in the death of target cell.

The main side effect of the photodynamic therapy resides in an enhanced light sensitivity of skin and eyes: patients need to be carefully protected against sunlight within six weeks and more. Another side effect consists in nausea and vomit caused in patients by the introduction of the PS in high amounts (Photodynamic Therapy. Cancer Facts, *National Cancer Institute, NIH, CancerNet*, 1994).

Both side effects are caused by a combination of two factors: an insufficient PS selectivity as respects target cells, and its excessive concentration in the patient tissues. Improvements in the efficiency of photodynamic damage (hereinafter referred to as "PDD") may be achieved by using the PS as a part of a composition.

There is a prior art composition based on microspheres was abto to enter the cell non-specifically by phagocytosis and penetrate into lysosomes. The application of the compositions of PS with microspheres results in the enhancement of PDD to the cell.

A drawback inherent in compositions with microspheres is that the photodynamic action of these compositions is not specific with respect to a cell type (Bachor, R., Shea, C. R., Gillies, R., and Hasan, T. Photosensitised destruction of human bladder carcinoma cells treated with chlorin $e_6$—conjugated microspheres. *Proc. Natl Acad. Sci. USA*, 88, 15 80–15 84, 1991).

Another prior art composition comprised chlorin $e_6$ with monoclonal antibodies. This prior art composition contains a component for the target cell identification, a PS carrier component and a PS itself. A disadvantage with such a composition lies in its ability to act on a target cell surface only, wherein PDD induced by the composition does not affect the most PDD-sensitive target cell compartments (Rakestraw, S. L., Tompkins, R. D., and Yarmush, M. L. Antibody-targeted photolysis: In vitro studies with Sn(IV) chlorin $e_6$ covalently bound to monoclonal antibodies using a modified dextran carrier. *Proc. Natl. Acad. Sci. USA*, 87, 4217–4221, 1990).

This disadvantage is avoided in a composition consisting of a PS, a PS carrier component and a component for target cell recognition and PS transport toward the interior of target cells by specific receptor-mediated endocytosis, said composition being the closest prior art composition to the present invention.

This composition is characterized by the presence of three components performing the same functions: a PS, a PS carrier component and a component for target cell recognition and PS transport toward the interior of the target cells by specific receptor-mediated endocytosis.

An insulin-BSA-chlorin $e_6$ composition, after binding to specific receptors on the surface of target cells, has the ability of receptor-mediated endocytosis and, accordingly, of transport toward the interior of cells where, after cell irradiation, the process of generating active oxygen species takes place, said species being a real cytotoxic agent in inducing PDD to the cell. This composition has an advantage over the aforementioned compositions with monoclonal antibodies or microspheres in that it is capable, through specific binding to cell surface receptors characteristic of this cell type, of being internalised by receptor-mediated endocytosis owing to which the formation of active photo-oxidation products occurs inside the cells near to damage-sensitive cell compartments. Although a number of the drawbacks associated with known compositions are removed, the composition lacks any special component to direct the PS transport within of target cells, e.g. transport into the most sensitive cell compartments for TDD. As a result, there is no efficient transport into these compartments, and PDD is not as great as it might be in the presence of said component for directing the transport inside the cells (Akhlynina, T. V., Rosenkranz, A. A., Jans, D. A., Sobolev, A. S. Insulin-mediated intracellular targeting enhances the photodynamic activity of chlorin $e_6$, *Cancer Res.*, 55, 1014–1019, 1995).

As indicated above, side effects are caused by two reasons: an insufficient PS selectivity as respects target cells and their excessive concentration in the patient tissues. Therefore, one of the directions in the development of this subject matter resides in the enhancement to the target cell PDD.

Enhancement of PDD to the target cell, while decreasing an acting PS concentration, is possible by using PS derivatives having other intracellular localisation which are most sensitive to the photodynamic action. As alluded to above, a prior art PDD method employed PS derivatives which penetrate into the cell by non-specific internalisation and localise in membrane components and lysosomes (Kessel, D. Determinants of photosensitisation by mono-L-aspartyl chlorin $e_6$. *Photochem. Photobiol.*, 49, 447–452, 1989). As also alluded to above, it is also possible to use PS conjugates with microspheres which enter the cell nonspecifically by phagocytosis and penetrate into lysosomes (Bachor, R., Shea, C. R., Gillies, R., and Hasan, T. Photosensitised destruction of human bladder carcinoma cells treated with chlorin $e_6$—conjugated microspheres. *Proc. Natl. Acad. Sci. USA*, 88, 1580–1584, 1991). Both known methods have the same disadvantage: PS and their derivatives may accumulate both in target cells and normal cells, that is to say, they are non-specific to a cell type (Aizawa, K., Okunaka, T., Kawabe, H., Yasunaka, Y., O'Hata, S., Ohtomo, N., Nishimiya, K., Konaka, C., Kato, H., Hayata, Y., and Saito, T. Localisation of mono-L-aspartyl chlorin $e_6$ (NPe$_6$) in mouse tissues. *Photochem. Photobiol.*, 46, 789–793, 1987).

Improvements in the PDD specificity may be achieved by the PS conjugation with a ligand having specific receptors on the target cell surface. For this purpose, PS compositions with monoclonal antibodies to these cells are proposed. Such an approach enables improvements in the PDD selectivity and efficiency at the expense of a specific recognition of target cells and binding of the compositions to the surface of these cells.

As alluded to above, a prior art method for the target cell PDD comprises a target cell PDD enhancement using PS—chlorin $e_6$ compositions with monoclonal antibodies (Rakestraw, S. L., Tompkins, R. D., and Yarmush, M. L. Antibody-targeted photolysis: In vitro studies with Sn(IV) chlorin e, covalently bound to monoclonal antibodies using a modified dextran carrier. *Proc. Nad. Acad. Sci. USA*, 87, 4217–4221, 1990): In accordance with this method, a composition comprising the PS is added to target cells, keeping the cell therewith and then exposed to light. Due to the composition properties, the PS is subjected to targeted transport into the cells as a part of the composition, the latter being bound to specific cell receptors. With such a method, plasma membranes are the main target for the PS. This is not optimal, however, since PDD does not extend to include much more sensitive intracellular targets—the nucleus or lysosomes (Alper, T. Cellular Radiobiology. *Cambridge Univ. Press*, Cambridge, 1979).

This disadvantage is avoided in the PDD method chosen by the applicant as the closest prior art method to the claimed one.

This method is characterized by the following essential features: a composition for PDD is introduced to target cells; then keeping the cells at a temperature of normal cellular vital activity with the result that target cells uptake a PS as part of the composition; and the PS is subsequently photo-activated (light-irradiated). This method, however, also suffers from disadvantages consisting in that, after cells have uptaken the PS, the latter, owing to the properties of the composition used, follows the way predetermined by the properties of the ligand—a component used for the recognition and receptor-mediated endocytosis of cells. In so doing, it will not necessarily find its way (or finds its way to a slight extent) into other PDD-sensitive cell parts (Akhlynina, T. V., Rosenkranz, A. A., Jans, D. A., Sobolev, A. S. Insulin-mediated intracellular targeting enhances the photodynamic activity of chlorin $e_6$. *Cancer Res.*, 55, 1014–1019, 1995).

SUMMARY OF THE INVENTION

It is an object of the present invention to provide compositions and method for causing photodynamic damage (PDD) to target cells to enable enhancement of target cell PDD owing to a composition capable of effective targeted transport of a photosensitiser (PS) within the target cells, thereby making it possible to improve safety and economy of the method.

This object is solved in a composition producing the target cell PDD in low concentrations due to the fact that the composition, in addition to a PS, a PS carrier component and a component which effects target cell recognition and receptor-mediated endocytosis, also comprises a component capable of effective targeted transport of the PS within the target cells, said composition resulting, due to the PS delivery to the most PDD-sensitive compartments, in the PDD enhancement.

BRIEF DESCRIPTION OF THE DRAWINGS

The various objects, advantages and novel features of the invention will be more readily apparent from the following detailed description when read in conjunction with the appended drawings, in which.

DETAILED DESCRIPTION OF THE INVENTION

In accordance with the present invention, a composition for causing photodynamic damage to target cells comprises a photosensitiser, a photosensitiser carrier component, a component which enables target cell recognition and transport of the photosensitiser toward the interior of the target cells by specific receptor-mediated endocytosis in these cells, and a component capable of effective targeted transport of the photosensitiser within the target cells, for example the transport into the most PDD-sensitive compartments of these cells. Individual components making up the composition may be covalently bound to each other and/or present in a "mechanical" mixture. Said components for directed intracellular transport represent substances which are capable of effective targeted transport of the composition or its components into the nucleus. Said components having the ability of targeted transport into the nucleus are hormones, proteins and peptides having an amino acid sequence of nuclear localisation signal (karyophilic sequence) and endosomolytic components which are capable of releasing compositions and the PS from endosomes (for example, some viruses, endosomolytic amphipathic peptides), which enables said transport to proceed more effectively into one of the most PDD-sensitive cell compartments—the nucleus. Lysosomes, for example, may serve as another sensitive compartment—an object of targeted transport inside the target cell. The PS carriers are used as various polymers, for example proteins, including recombinant polypeptides. Components which effect target cell recognition (binding with them) and direct transport inside the cells by receptor-mediated endocytosis are internalizable ligands, in particular peptide hormones (insulin, somatotropin, prolactin, etc.), lectins (concanavalin A, ricin, wheat germ agglutinin, etc.), other protein (transferrin, ferritin) and protein-free (sugars, low-molecular hormones) components. Various molecules capable, when exposed to light, of generating active oxygen species (porphyrins, phthalocyanines, etc.) may be used as the PS.

For a targeted delivery of the PS into the eukaryotic cell nuclei, we use a composition consisting of the following components: PS chlorin $e_6$, a carrier component—bovine serum albumin (BSA), a component for target cell recognition and PS transport by receptor-mediated endocytosis—internalizable ligand, insulin, and a component capable of effective targeted transport of the PS within target cells—a karyophilic sequence of the SV40 large T-antigen ensuring targeted intracellular transport of the composition into the nucleus. The present composition has the following structure: chlorin $e_6$, a karyophilic sequence and insulin are covalently bound to a BSA carrier protein.

The composition comprises a chemically synthesized karyophilic sequence of the SV40 large T-antigen (peptide PI 101). Peptide PI 101 comprises a karyophilic sequence.

Another composition has a similar structure but, in this case, βgalactosidase from *E. coli* serves as a carrier protein. A chimeric protein P10 is prepared in which a carrier protein (βgalactosidase) is fused with said component capable of effective targeted transport of the PS within target cells, namely with the karyophilic sequence of the SV40 large T-antigen; a galactosidase part of protein P10 acts as a carrier and ensures an intracellular transport of the composition into the target cell nuclei; to this recombinant protein, the PS (chlorin $e_6$) and insulin are covalently bound. It is shown that the presence of said karyophilic sequence leads to a significant enhancement of the target cell PDD. However, even such composition is not able to be fully transported into the cell nuclei since it comprises insulin and, therefore, such a composition, after being internalised into the target cell by receptor-mediated endocytosis, appears to be enclosed within endosomes. To leave endosomal vesicles, the composition should comprise one more component for a targeted transport of the PS inside the target cells, namely a component enabling exit of the composition from endosomes.

There has been also known a possibility for the disintegration of endocytotic vesicles (for example, endosomes) by means of adenoviruses (Fitz-Gerald, J. D. P., Padmanabhan, R., Pastan, L, and Willingham, M. C. Adenovirus-induced release of epidermal growth factor- and Pseudomonas toxin into the cytosol of KB cells during receptor-mediated endocytosis. *Cell*, 32, 607–617, 1983).

A further composition is provided with an endosomolytic component—a nonreplicating mutant virus type which enables exit of the compositions from endosomes (human adenovirus, serotype 5, strain dl-312) (Jones, N., Shenk, T. An adenovirus type 5 early gene function regulates expression of other early viral genes. *Proc. Natl. Acad. Sci. USA*, 76, 3665–3669, 1979).

A subsequent intracellular PS transport into the nuclei is carried out owing to the fact that the composition comprises a karyophilic sequence (as part of the protein P10 composition).

The present object is also solved owing to the enhancement of PDD by introducing the PS to the cells in the composition having the ability of a targeted transport of the PS within target cells; keeping them at a temperature of normal vital activity of the cells; and subsequent exposure of the cells to light.

As a result of such application of the composition, the PS is subjected to targeted delivery into target cells, bound to specific receptors on the target cells, transferred toward the interior of the target cells by receptor-mediated endocytosis and transported into the most PDD-sensitive cell compartments, and the PS photo-activation may be done most efficiently. In so doing, the nuclei are employed as sensitive compartments.

In accordance with the present invention, a method for causing photodynamic damage to target cells includes the use of those compositions which comprise a photosensitiser, a photosensitiser carrier component, a component which enables target cell recognition and transport of the photosensitiser toward the interior of the target cell by specific receptor-mediated endocytosis, and a component capable of effective targeted transport of the photosensitiser within target cells. The method for causing photodynamic damage to target cells also includes the use of those compositions which have the ability of effective targeted transport into the cell nucleus and compositions having the ability of releasing the photosensitiser from endocytotic compartments.

When solving the object in hand, it was taken into account that the photodynamic effect of an overwhelming majority of PS (porphyrins, phthalocyanines) was due to the generation of the so-called "active oxygen species" (singlet oxygen, some oxygen free radicals, etc.) known to be properly toxic agents. It was also known that an average range of said active oxygen species in the cell did not exceed a one hundredth of a micron (Bekker, G. O., et al. Introduction into photochemistry of organic compounds. 1976, p. 326). Because of this, cellular membranes in which the PS localise were the main target for the PS. The enhancement of PDD while decreasing an acting PS concentration was achieved by using the PS as part of the composition comprising components enabling a targeted transport of the PS into the most PDD-sensitive compartments of target cells, damage to which is critical for cell survival. Delivery of the PS to PDD-sensitive target cell compartments is carried out after the PS as part of the composition has been bound to the target cell and then absorbed by the latter. To prepare compositions which could be bound to specific receptors of the target cells and then transported into said target cells by receptormediated endocytosis, conjugation of the PS with a ligand having such receptors on the target cell surface is performed. Ligands such as, for example insulin, somatotropin and many others, after binding to their respective receptors on the cell surface, penetrate into the interior of the cells by receptor-mediated endocytosis; and it is possible to accomplish a targeted intracellular transport of the composition—receptor complex into the most sensitive cell compartments (Backer, J. M., Kahn, O. R., and White, M. F. Tyrosine phosphorylation of the insulin receptor during insulin-stimulated internalisation in rat hepatoma cells. *J. Biol. Chem.*, 264, 1694–1701, 1989).

If the component for a targeted transport is bound to a ligand penetrating into the cell by receptor-mediated endocytosis, it is possible, through a targeted delivery, that an intracellular PS localisation be replaced and said PS be delivered to more sensitive cell compartments, thereby enabling decrease in an acting PS concentration necessary to be administered to achieve the effect.

A method for causing photodynamic damage to target cells using compositions for enhancing said photodynamic damage to target cells is carried out as follows.

Components in the composition are synthesized; the composition is prepared to be suitable for a selected type of target cells; applied to an object containing target cells for PDD; keeping at a temperature of normal cellular vital activity, and a photosensitiser is subjected to photoactivation.

The possibility to carry out the method for causing photodynamnic damage to target cells using compositions for causing photodynamic damage to target cells of the photosensitiser is confirmed by the following Examples.

EXAMPLE 1

Synthesis of (BSA)-(chlorin $e_6$)-(PI 101)-insulin Composition

Step 1. Preparation of chlorin $e_6$

Chlorin $e_6$ was prepared from nettle leaves (Urtica dioica L.) in accordance with a standard method of Fischer (Fischer, H., Stern, A. Die Chemie des Pyrrols. Leipzig: Akad. Verl., 2, 478S, 1940) with modifications (Hynninen, P. H., Chlorophylls. IV. Preparation and purification of some derivatives of chlorophylls a and b. *Acta Chem. Scand.,* 27, 1771–1780, 1973).

Step 2. Synthesis of (BSA)-(chlorin $e_6$) Conjugate

BSA-chlorin $e_6$, conjugation was performed in Na-phosphate buffer (10 mM, pH 7.5) by means of cyclohexyl-3-(2-morpholinoethyl) carbodiimide meto-4-toluenesulphonate (CDI) (Serva). The (BSA):(chlorin $e_6$):(CDI) ratio was 1:30:300. The reaction was carried out for 18 hours at 4° C. Thereafter, dialysis against the same buffer was performed.

Step 3. Activation of (BSA)-(chlorin $e_6$) Conjugate with 3-maleimidebenzoyl Hydroxysuccinimide Ester (MBS)

To activate $NH_2$-groups of BSA for a further conjugation, the reaction with MBS (Sigma) was carried out in the same Na-phosphate buffer at the (BSA):(MBS) ratio of 1:100. MBS was diluted in dimethyl formamide and added to the (BSA)-(chlorin $e_6$) conjugate. A mixture was left for 1 hour at room temperature followed by removal of MBS residue with dialysis against Na-phosphate buffer (10 mM, pH 7.5; 0.5 mM EDTA).

Step 4. Synthesis of (BSA)-(chlorin $e_6$)-(PI 101)-insulin Composition

Peptide PI 101 at its C-end contains cysteine, via which SH-groups conjugation of peptide with MBS-activated BSA amino groups may be performed. When mixing the peptide with MBS-activated (BSA)-(chlorin $e_6$) conjugate under anaerobic conditions ((BSA)-(chlorin $e_6$) and peptide ratio is 1:30), a covalent binding of the peptide to BSA occurs. The reaction was carried out for 3 hours at room temperature followed by removal of the peptide residue with dialysis against Na-phosphate buffer (10 mM, pH 7.5; 0.5 mM EDTA).

Step 5. Activation of Insulin by Sulfosuccinimide 4-(maleimido methyl)cyclohexane-1-carboxylate (Sulfo-SMCC)

Insulin and sulfo-SMCC (Pierce) were diluted in Na-phosphate buffer (10 mM, pH 7.5) and mixed at a 1:1.5 ratio. The reaction was carried out for 30 minutes at 37° C. Thereafter, dialysis against Na-phosphate buffer (10 mM, pH 7.5; 0.5 mM EDTA) was performed.

Step 6. Reducing SH-groups of BSA by Means of Dithiothreitol (DTT)

To (BSA)-(chlorin $e_6$)-(PI 101), DTT (Sigma) was added to a final concentration of 50 mM and incubated for 30 minutes at 37° C. followed by dialysis against Na-phosphate buffer (10 mM, pH 7.5; 0.5 mM EDTA) was performed.

Step 7. Preparation of (BSA)-(chlorin $e_6$)-(PI 101)-insulin Composition

Insulin and (BSA)-(chlorin $e_6$)-(PI 101) obtained as described in Steps 4 and 5, respectively, were mixed under anaerobic conditions at the 15:1 ratio. Incubation was carried out for 18 hours at 4° C. Thereafter, the composition was purified by column chromatography on Sephacryl S-300 eluting with 25 mM HEPES, pH 7.5; 50 mM NaCl.

After the completion of all the conjugation steps, polyacrylamide gel electrophoresis according to a method of Laemmli was performed to determine molecular weight of the composition so obtained.

EXAMPLE 2

Determining Localisation of (BSA)-(chlorin $e_6$)-(PI 101 )-insulin Composition in Human Hepatoma PLC/PRF/5 Cells In order to reveal localisation of the (BSA)-(chlorin $e_6$)-(PI 101)-insulin composition in cells, 2',7'-dichlorofluorescein diacetate was used. When incubating with cells at 37° C., this substance penetrates into the cells and there it is deacetylated by intracellular esterases. If the production of active oxygen species occurs in the place of 2',7'-dichlorofluorescein localisation, then 2',7'-dichlorofluorescein, while interacting with these species, converts into fluorescent 2',7'-dichlorofluorescein (Patel, A. K., Hallet, M. B., and Campbell, A. K. Threshold responses in production of reactive oxygen metabolites in individual neutrophils detected by flow cytometry and microfluorimetry. *Biochem. J,* 248, 173–180, 1987). Because it is known that the range of active oxygen species is very small, the composition localisation coincides with that of active oxygen species generated by this composition after irradiation of the cells and, therefore, in the presence of 2',7'-dichlorofluorescein diacetate it is possible to reveal both the place of the composition location in the cell and the place of generation of those toxic products which give rise to a PS-caused PDD.

Human hepatoma PLC/PRF/5 cells were incubated with 100 nM (BSA)-(chlorin $e_6$)-(PI 101)-insulin composition for 18 hours at 37° C. in RPMI-1640 medium containing 2 mg/ml BSA, 25 mM HEPES, pH 7.5. Upon the completion of incubation, cells were washed with the same medium, incubated for 5 minutes with 2.5 $\mu$M 2',7'-dichlorofluorescein diacetate, washed out from the latter and exposed to light of a slide projector followed by the recording of a fluorescence distribution in cells by means of cooled CDD camera AT-200 (Photometrics). As can be seen in FIG. 1, the (BSA)-(chlorin $e_6$-(PI 101T)-insulin composition penetrates into the cell and the nuclei much more effectively than the (BSA)-(chlorin $e_6$)-( PI 101T)-insulin composition (peptide PI 101 T differs from peptide PI 101 in that $Thr^7$ was substituted for $Lys^7$), wherein the transport of the compositions into the cell is carried out via insulin receptors, which is proved by the absence of fluorescence in cells during their co-incubation with the composition and a 100-fold excess of free insulin.

EXAMPLE 3

Synthesis of (P10)-insulin-(chlorin $e_6$) Composition

For the preparation of the titled composition, a recombinant protein P10 was used as the carrier protein (Ribs, H. -P., Jans, D. A., Fan, H., and Peters, R. The rate of nuclear cytoplasmic protein transport is determined by the casein kinase II site flanking the nuclear localisation sequence of SV40 large T-antigen. *EMBO J.,* 10, 633–639, 1991). Protein P10 is a product of chimeric gene in which a karyophilic sequence of the SV40 large T-antigen was attached to a sequence encoding a bacterial protein β-galactosidase from *E. coli.* A bacterial β-galactosidase was used as control.

Step 1. Isolation of Proteins P10 and β-galactosidase

To prepare a chimeric gene P10 and β-galactosidase, *E. coli* cell-expressed plasmids pDJ87 and pDJ148 were used, respectively.

For each protein, a corresponding *E. coli* culture was grown in LB-broth (Sigma) with Na-ampicillin and isopropyl-β-thiogalactoside (SibEnzyme) as a protein expression inducer. After centrifugation of bacterial mass and ultrasound lysis, the suspension was re-centrifuged and supernatant applied to affinity column using p-aminobenzyl 1-thio-β-D-galactopyranoside (Sigma) as sorbent. After washing the column with 20 mM Tris-HCl, pH 7.4; 10 mM $MgCl_2$; 1.6 M NaCl (Sigma); 10 mM 2-mercaptoethanol (to remove other protein impurities), the protein to be isolated was eluted with borate buffer (0.1 M, pH 10.05; 10 mM 2-mercaptoethanol). The presence of protein in fractions was determined by the colour reaction with o-nitrophenyl-β-D-galactopyranoside (Sigma) (Pardee, A. B., Jacob, F., and Monod, J. The genetic control and cytoplasmic expression of "inducibility" in the synthesis of β-galactosidase by *E. coli.* *.l. Mol. Biol.,* 1, 165, 1959). After dialysis in phosphate buffer (10 mM, pH 7.0; 10 mM 2-mercaptoethanol), protein was concentrated by ultrafiltration. A protein concentration was determined by absorption at 280 nm.

Step 2. Preparation of Chlorin $e_6$

Chlorin $e_6$ was prepared as described in Example 1.

Stems 3. Preparation of Aminochlorin

CDI and diaminohexane (Sigma) was added to chlorin $e_6$ in 5 mM Na-phosphate buffer, pH 7.5. The (chlorin $e_6$):(CDI):diaminohexane ratio was 1:100:100. The reaction was carried out overnight at 4° C. Thereafter, excessive CDI and diaminohexane were removed by dialysis in Na-phosphate buffer (10 mM, pH 7.0).

Step 4. Preparation of Citraconated Insulin

To prepare conjugates with ligand having specific internalized receptors, insulin modified with citraconic anhydride was used. Insulin—citraconic anhydride interaction results in the protection of the terminal amino group of insulin which participate in the interaction with receptors; therefore, the amino groups of lysine located in the middle of polypeptide chain are able to be modified after insulin citraconation. Modification of insulin with citraconic anhydride was carried out according to a method of Shechter (Shechter, Y., Schlessinger, J., Jacobs, S., Chang, K. J., and Cuatrecasas, P. Fluorescent labeling of hormone receptors in viable cells: Preparation and properties of highly fluorescent derivatives of epidermal growth factor and insulin. *Proc. Natl. Acad. Sci. USA,* 75, 2135–2139, 1978).

Step 5. Synthesis of (P 10)-(chlorin $e_6$) and (β-galactosidase)-(chlorin $e_6$) Conjugates CDI was also used for the conjugation of proteins with aminochlorin $e_6$. The reaction was carried out in Na-phosphate buffer (10 mM, pH 7.0) at the protein:(aminochlorin $e_6$):(CDI) ratio of 1:30 300. The conjugates were subjected to dialysis in order to be purified from unbound aminochlorin $e_6$ and excessive CDI.

Step 6. Synthesis of (P 10)-(chlorin $e_6$) and (β-galactosidase)-insulin-(chlorin $e_6$) Compositions Insulin modified with citraconyl groups was covalently bound to (P10)-(chlorin $e_6$) and (β-galactosidase)-(chlorin $e_6$) conjugates by means of a bifunctional cross-linking agent, N-succinimidyl-3-(2-pyridildithio)-propionate (SPDP) (Sigma), according to the procedure disclosed by Jung et al. (Jung, G., Kohnlein, W., and Luders, G. Biological activity of antitumor protein neocarcinostatin coupled to a monoclonal antibody by N-succinimidyl-3-(2-pyridilthio)-propionate. *Biochem. Biophys. Res. Commun.,* 101, 599–606, 1981). Insulin was taken at a concentration exceeding 15-fold that of the conjugate, based on protein. Following incubation and dialysis in Na-phosphate buffer (10 mM, pH 7.0), citraconyl groups were removed by acidification followed by extraction of compositions, as disclosed by Shechter et al. Thereafter, the compositions were subjected to dialysis in Na-phosphate buffer (10 mM, pH 7.0).

To determine the number of bound insulin molecules per the composition molecule, electrophoresis was performed in a 5% polyacrylamide gel according to a method of Laemmli (Laemmli, U. K. Cleavage of structural proteins during the assembly of the head of bacteriophage T4. *Nature,* 227, 680–685, 1870). The protein:(chlorin $e_6$):insulin ratio in the compositions was found to be 1:5:8.

EXAMPLE 4

Figure 1A:
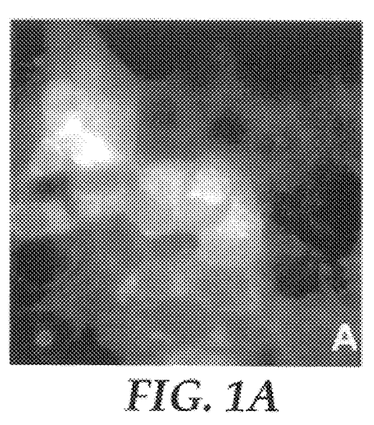
FIG. 1 shows an intracellular distribution of oxygen active species after irradiation of cells which is determined by the formation of 2',7'-dichlorofluorescein. PLC/PRF/5 cells were incubated in the presence of 100 nM (BSA)-(PI 101)-insulin-(chlorin $e_6$) (A) and (BSA)-(PI 101T)-insulin-(chlorin $e_6$) (B) compositions for 18 hours at 37° C. with or without a 100-fold excess of insulin (C and D), respectively. After incubation, the cells were washed, incubated for 5 minutes at 37° C. with 2',7'-dichlorofluorescein diacetate, re-washed and exposed to light of a slide projector.
Figure 1B:
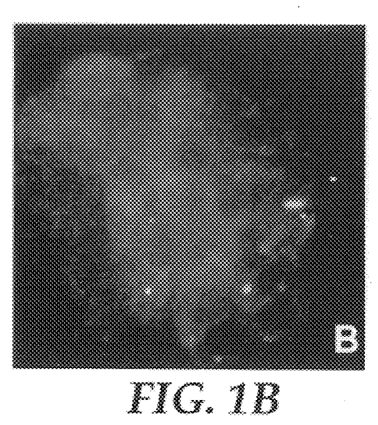
Figure 1C:
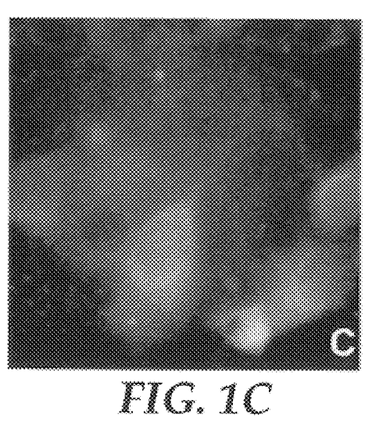
Figure 1D:
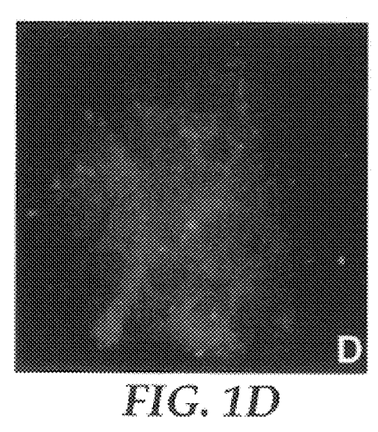
Figure 2:
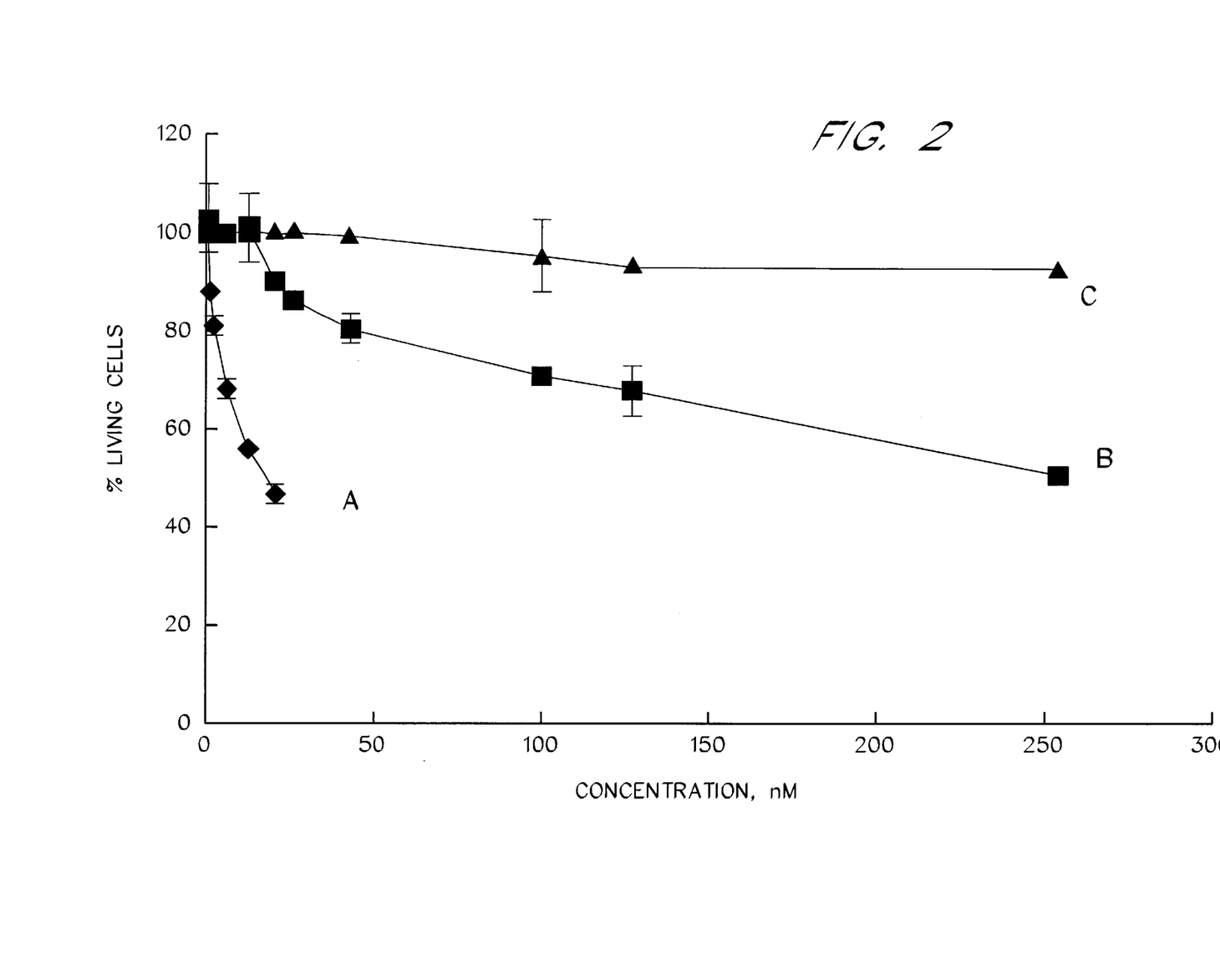
FIG. 2 shows survival rate of human hepatoma PLC/PRF/5 cells plotted against concentration of (P10)-insulin-(chlorin $e_6$) and (β-galactosidase)-insulin-(chlorin $e_6$) compositions and chlorin $e_6$ at the irradiation dose of 12.3 kJ/m². A stands for (P10)-insulin-(chlorin $e_6$); B stands for (β-galactosidase)-insulin-(chlorin $e_6$); C stands for chlorin $e_6$.
Figure 3:
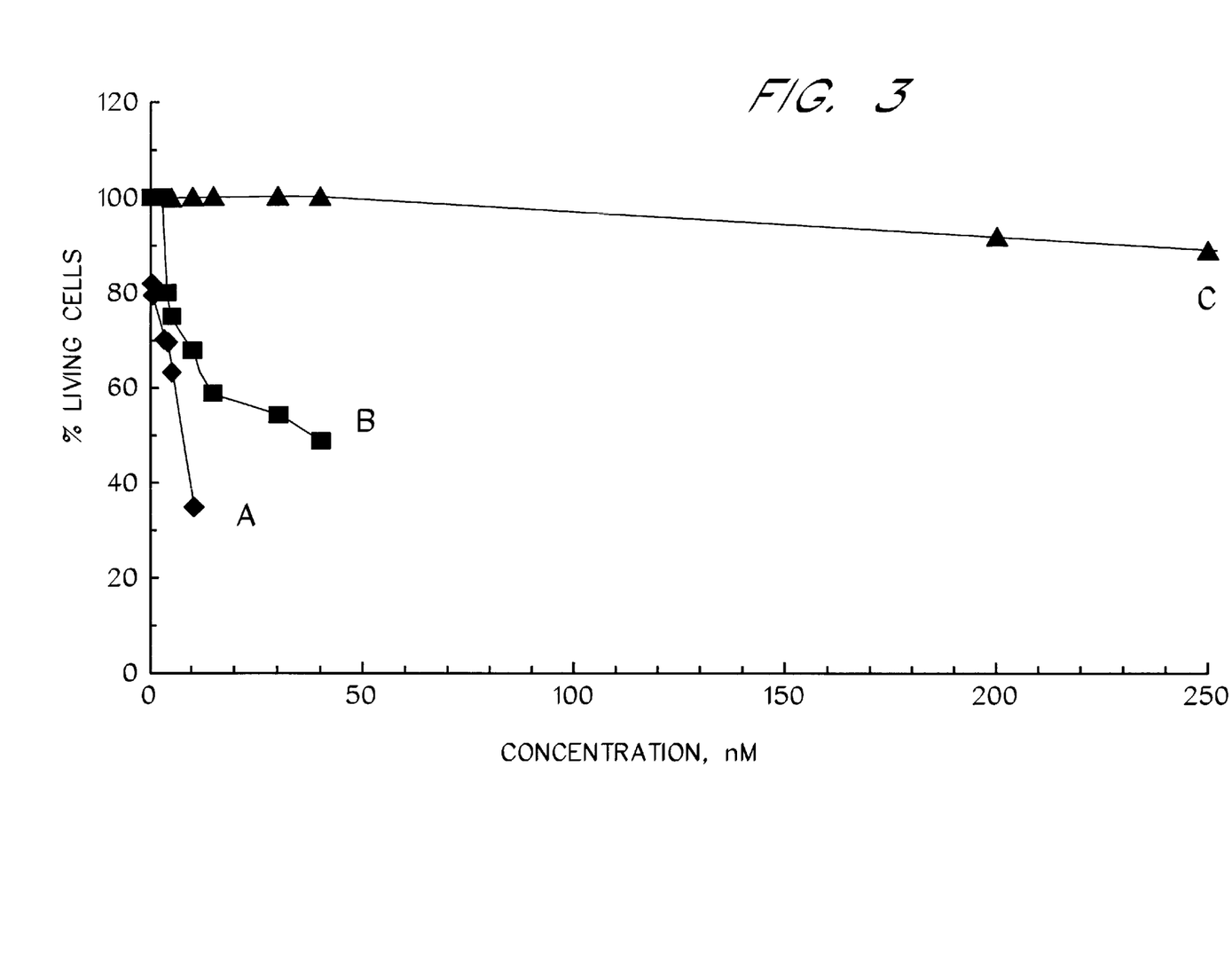
FIG. 3 shows survival rate of human hepatoma PLC/PRF/5 cells plotted against concentration of (P10)-insulin-(chlorin $e_6$), (β-galactosidase)-insulin-(chlorin $e_6$) compositions and chlorin $e_6$ at the irradiation dose of 96 kJ/m². A stands for (P10)-insulin-(chlorin $e_6$); B stands for (β-galactosidase)-insulin-(chlorin $e_6$); C stands for chlorin $e_6$.

PDD of Human Hepatoma PLC/PRF/5 cells Using (P10)-insulin-(chlorin $e_6$) Composition Use of the composition in human hepatoma cells showed that the presence in the composition of a sequence permitting transport of the composition into the nucleus, enhanced to a greater extent the photodynamic action of chlorin $e_6$ present in the composition. At the irradiation dose of 12.3 $kJ/m^2$, the $EC_{50}$ value (concentration of a semi-maximal effect) was found to be 17 nM for the (P10)-insulin-(chlorin $e_6$) composition, 319 nM for the control (β-galactosidase)-insulin-(chlorin $e_6$) composition and 11,500 nM for free chlorin $e_6$. At the irradiation dose of 96 $kJ/m^2$, the $EC_{50}$ value was found to be 7.2. nM for the (P10)-insulin-(chlorin $e_6$) composition, 38 nM for the (β-galactosidase)-insulin-(chlorin $e_6$) composition and 350 nM for chlorin $e_6$. Survival rate of human hepatoma PLC/PRF/5 cells plotted against concentration of compositions and chlorin $e_6$ is depicted in FIGS. 2 and 3.

EXAMPLE 5

Method for Producing (P10)-insulin-(chlorin $e_6$) Composition+Endosomolytic Component (adenovirus) and (β-galactosidase)-insulin-(chlorin $e_6$) Composition+Endosomolytic Component (adenovirus)

To escape compositions from intracellular endosomes into the cytosol, we used human adenovirus Ads d1-312. To this end, cells were incubated with a (P10)-insulin-(chlorin $e_6$) or (β-galactosidase)-insulin-(chlorin $e_6$) composition together with adenovirus. On the second day after incubation, cells were washed out with RPMI-1640 medium supplemented with 2 mg/ml BSA, 25 mM HEPES, pH 7.5 and incubated with said compositions or with said compositions in the presence of virus. Concentration of the compositions in the incubating medium was 20 nM, that of adenovirus—$3.66 \times 10^{10}$ virions/ml. In the experiments with adenovirus, a preliminary incubation for 1 hour at 4° C. was carried out to enable an efficient binding of virus and compositions to their receptors and subsequent simultaneous beginning of the internalisation cycle of insulin and adenovirus receptors after the cell transfer to 37° C. Following 18 hour incubation at 37° C., the cells were washed using the same medium.

EXAMPLE 6

Figure 4:
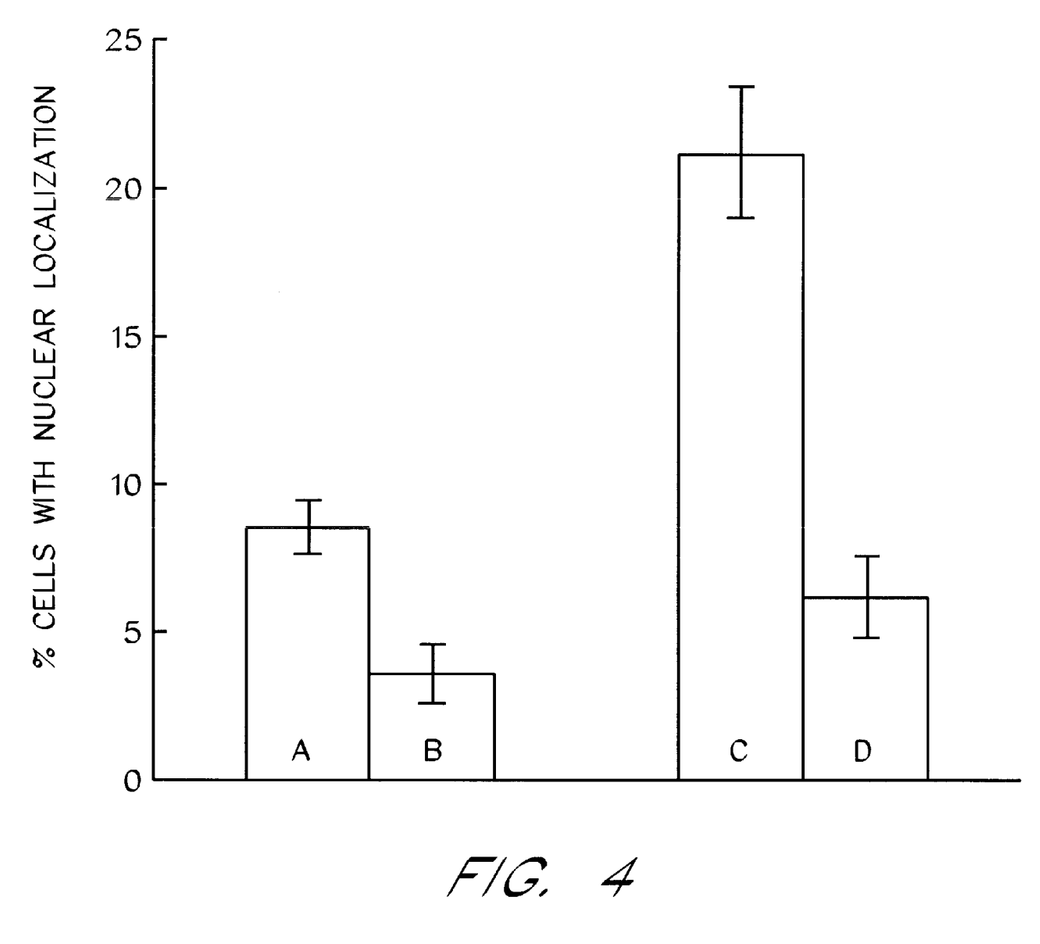
FIG. 4 shows the comparison of localisation of oxygen active species after photoactivation of compositions in human hepatoma PLC/PRF/5 cells. A stands for (P10)-insulin-(chlorin $e_6$; B stands for (β-galactosidase)-insulin-(chlorin $e_6$); C stands for (P10)-insulin-(chlorin $e_6$)+(human adenovirus, serotype 5, strain d1-312); D stands for (β-galactosidase)-insulin-(chlorin $e_6$) +(human adenovirus, serotype 5, strain d1-312). Localisation was determined by the formation of 2',7'-dichlorofluorescein.

Localisation of Compositions (P10)-insulin-(chlorin $e_6$ Composition+Endosomolytic Component (adenovirus) and (β-galactosidase)-insulin-(chlorin $e_6$)+Endosomolytic Component (adenovirus) in Human Hepatoma PLC/PRF/5 cells During incubation of human hepatoma PLC/PRF/5 cells with the (P10)-insulin-(chlorin $e_6$) composition in the presence of adenovirus Ad5 d1-312, the number of cells with a primary localisation of the composition in the nucleus increased by 148%, which was 3.5 times as many as for the (β-galactosidase)-insulin-(chlorin $e_6$) composition (FIG. 4).

INDUSTRIAL APPLICABILITY

The claimed composition for causing photodynamic damage to target cells and method for causing photodynamic damage to target cells may be applied in biotechnology, cellular and molecular biology when developing methods in experimental medicine and pharmacology.

What is claimed is:

1. A composition for causing photodynamic damage to target cells, comprising:
    a photosensitizer;
    a carrier for the photosensitizer;
    an endosomolytic component;
    a first component which enables target cell recognition and transport of the photosensitizer toward the interior of the target cell by specific receptor-mediated endocytosis; and
    a karyophilic moiety for targeted transport of the photosensitizer to the nucleus of the target cells;
    wherein the carrier is conjugated to the karyophilic moiety, the photosensitizer and the first component.

2. The composition according to claim 1, wherein said endosomolytic component is adenovirus.

3. The composition according to claim 2, wherein said adenovirus is human adenovirus, type 5, strain d1-312.

4. The composition according to claim 1, wherein said carrier for the photosensitizer is a polymer.

5. The composition according to claim 4, wherein said polymer is a protein.

6. The composition according to claim 5, wherein said protein is bovine serum albumin.

7. The composition according to claim 5, wherein said protein is a recombinant polypeptide.

8. The composition according to claim 7, wherein said recombinant polypeptide is a bacterial β-galactosidase fused with said karyophilic moiety, said moiety being a karyophilic sequence of the SV40 large T-antigen.

9. The composition according to claim 1, wherein said first component which enables target cell recognition and transport of the photosensitizer toward the interior of the target cell by specific receptor-mediated endocytosis is an internalizable ligand.

10. The composition according to claim 9, wherein said internalizable ligand is a peptide hormone.

11. The composition according to claim 10, wherein said peptide hormone is insulin.

12. The composition according to claim 1, wherein said photosensitizer is chlorin e6.

13. A method for causing photodynamic damage to target cells, comprising the steps of:
    contacting the target cells with a composition of claim 1 so as to produce a population of treated cells by targeted transport of said photosensitizer into the target cells;
    keeping the population of treated cells at a temperature of normal vital activity of cells for a period of time; and
    exposing the population of treated cells to light, thereby causing photodynamic damage to the target cells.

14. The method according to claim 13, wherein said composition for causing photodynamic damage is directed to the nucleus of the target cells by targeted transport.

15. The method according to claim 13, wherein said composition for causing photodynamic damage is released from endocytotic compartments.

16. The composition of claim 1, wherein said karyophilic component is covalently bound to the carrier.

17. The composition of claim 1, wherein the first component is bound to the photosensitizer.

* * * * *